(12) United States Patent
Cahen et al.

(10) Patent No.: US 7,488,991 B2
(45) Date of Patent: Feb. 10, 2009

(54) MOLECULAR CONTROLLED SEMICONDUCTOR DEVICE

(75) Inventors: David Cahen, Rechovot (IL); Igor Lubomirsky, Petach-Tikva (IL)

(73) Assignee: Yeda Research And Development Co. Ltd., Rechovot (IL)

( * ) Notice: Subject to any disclaimer, the term of this patent is extended or adjusted under 35 U.S.C. 154(b) by 25 days.

(21) Appl. No.: 11/292,370

(22) Filed: Dec. 2, 2005

(65) Prior Publication Data

US 2006/0118903 A1  Jun. 8, 2006

Related U.S. Application Data

(60) Provisional application No. 60/632,536, filed on Dec. 3, 2004.

(51) Int. Cl.
*H01L 29/74* (2006.01)
(52) U.S. Cl. ............ 257/106; 257/104; 257/494; 257/E29.013; 257/E29.019; 257/E29.338; 257/E29.335; 436/151
(58) Field of Classification Search ............ 257/494, 257/E29.013, E29.019, E29.338, 104, 106, 257/199, E29.335; 436/151
See application file for complete search history.

(56) References Cited

U.S. PATENT DOCUMENTS

| | | | | |
|---|---|---|---|---|
| 4,777,019 A | * | 10/1988 | Dandekar | ............ 422/82.02 |
| 5,541,426 A | * | 7/1996 | Abe et al. | ............ 257/170 |
| 6,433,356 B1 | | 8/2002 | Cahen et al. | |
| 6,791,161 B2 | * | 9/2004 | Hamerski | ............ 257/603 |

OTHER PUBLICATIONS

Gartsman et al. "Molecular Control of A GaAs Transistor", Chemical Physics Letters, 283: 301-306, 1998.
Ashkenasy et al. "Molecular Engineering of Semiconductor Surfaces and Devices", Accounts of Chemical Research, 35(2): 121-128, 2002.

* cited by examiner

*Primary Examiner*—Long K Tran

(57) ABSTRACT

A semiconductor sensing device for sensing presence, absence or level of species-of-interest in the environment is disclosed. The semiconductor sensing device comprises at least one layer of molecules deposited thereon. The molecules are electrically-responsive to the species-of-interest in a manner such that when the molecules interact with the species-of-interest, a reverse breakdown voltage characterizing the semiconductor sensing device is modified.

44 Claims, 5 Drawing Sheets

MOLECULAR CONTROLLED SEMICONDUCTOR DEVICE

RELATED APPLICATION

This application claims benefit of U.S. Provisional Patent Application No. 60/632,536, filed on Dec. 3, 2004, the content of which is hereby incorporated by reference.

FIELD AND BACKGROUND OF THE INVENTION

The present invention relates to a semiconductor device and, more particularly, to a molecular controlled semiconductor sensing device.

Semiconducting materials are well known and include n-type and p-type semiconductors, so named because either they have an excess of electrons ("−"; n-type semiconductor) or a deficit of electrons than what is necessary to complete a lattice structure ("+"; p-type semiconductor). The extra electrons in the n-type material and the holes (deficit of electrons) left in the p-type material serve as negative and positive charge carriers, respectively. Semiconductor devices typically include at least one p-n junction, which is a border region between an n-type and p-type semiconductor. The p-n junction possesses properties, which can be used in many electronic applications, such as diodes, transistors, memory media and the like.

A diode is an electronic device that allows current flow (i.e., electronic conduction) in one direction but prevents current flow (i.e., is insulating) in the opposite direction. Commonly, the conductive and insulating states of a diode are referred to as a "forward bias" and "reverse bias" effects, respectively, where the term "bias" corresponds to the application of electric voltage to the p-n junction.

In forward bias, the holes in the p-type region and the electrons in the n-type region are pushed towards the p-n junction. Application of a forward bias is by connecting the p-type region to a positive terminal of a voltage source and the n-type part to a negative terminal of the voltage source. With such voltage configuration, the positive charge applied to the p-type region repels the holes, while the negative charge, applied to the n-type region, repels the electrons. This reduces the junction barrier, allowing the electrons to overcome this barrier and enter the p-type region. Once inside the p-type region, the electrons make their way to the positive terminal of the power supply, hence generating an electric current.

In reverse bias, the p-type region is connected to the negative terminal and the n-type region is connected to the positive terminal of the power supply, thus pulling the holes in the p-type and the electrons in the n-type away from the p-n junction. This effectively widens the p-n junction, increasing the electrical resistance to the flow of electrons. Up to a certain voltage, commonly referred to as the breakdown voltage, regular diodes practically prevent current flow therethrough. By exceeding the breakdown voltage, a regular diode is destroyed due to excess current and overheating.

A Zener diode is a diode device especially designed to have a greatly reduced breakdown voltage, also known as the Zener voltage, named after C. M. Zener (1905-1993). A Zener diode contains a heavily doped p-n junction allowing electrons to tunnel from the valence band of the p-type material to the conduction band of the n-type material. A current-voltage curve characterizing the Zener diode comprises a region of forward current at a forward voltage (about 0.7 volts for silicon diode), a region of reverse or breakdown current at the Zener voltage and a flat region of small (practically zero) current therebetween. Thus, upon application of a reverse bias, the Zener diode exhibits a controlled breakdown and lets current flow in a manner such that the voltage across the Zener diode is kept at the Zener voltage. The breakdown voltage of a Zener diode can be accurately controlled in the doping process of the semiconductor materials forming the p-n junction.

An avalanche diode is another diode device designed to provide a breakdown current. It this device, the breakdown is by impact ionization rather than by the Zener effect. When no or small reverse voltage is applied to the avalanche diode, thermal energy results in formations of a few electron-hole pairs in the depletion region of the p-n junction. When a sufficient reverse voltage (i.e., above the breakdown voltage) is applied across the p-n junction, the electrons accelerate in the electric field, collide with the atoms of the semiconductor lattice, and rupture their covalent bonds to form more pairs. The released electrons also accelerate in the electric field, resulting in a chain or avalanche effect of carrier multiplication in which further electron-hole pairs are released. The avalanche effect releases an almost unlimited number of carriers so that the avalanche diode essentially becomes a short circuit. The current flow in this region is limited only by an external series current-limiting resistor. Once the reverse voltage is removed, all the charge carriers return to their normal energy values and momenta.

A Schottky diode is a diode device which, unlike the p-n junction of a conventional diode, has a metal-semiconductor junction in which the work function of the metal and the band gap of the semiconductor are selected to reduce the voltage across the junction. Such junction is termed Schottky barrier, after Walter H. Schottky (1886-1976).

A field effect transistor (FET) is a semiconductor device having a source electrode, a drain electrode, a gate electrode and a channel, which is separated from the gate electrode by a thin isolating layer. The channel has semiconducting properties (either n-type or p-type semiconducting properties) such that the density of charge carriers therein can be varied. When no voltage is applied to the gate electrode, the channel does not contain any free charge carriers and is essentially an insulator. Upon application of a certain level of voltage to the gate electrode, an electric field, generated between the channel and the gate, attracts charge carriers (electrons or holes) from the source electrode and the drain electrode, and the channel becomes conductive.

Semiconductor materials and devices can be used as transducers in sensing applications whereby semiconductor materials are combined with a sensing element responsive to chemicals or energy. For example, in U.S. Pat. No. 4,777,019, the contents of which are hereby incorporated by reference, small monomers of macromolecules are directly introduced into the surface layer of a semiconductor, to thereby form a biosensor having an improved signal to noise ratio. The use of semiconductor materials as transducers in sensing devices is an attractive option because sensing devices employing other transducers (e.g., electrochemical, piezoelectric or optical transducers) suffer from various limitations, including high cost, complexity and/or bulkiness. Contrarily, the combination of semiconductors with sensing molecules enjoys the selectivity, sensitivity and versatility of molecular synthesis as well as the benefits of robustness and proven technology of today's optoelectronics (to this end see, e.g., "Physics, Chemistry, and Technology of Solid State Gas Sensor Devices", by A. Mandelis and C. Christofides, Wiley, New York, 1993).

Generally, the design of sensing devices is aimed at achieving sensitivity, selectivity, robustness and versatility. However, combining these qualities in the process of designing an electronic sensor was proven very difficult and many of today's sensors are optically in nature, requiring a detector system to couple to electronic circuits. The use of molecules (e.g., organic molecules) as sensing elements in electronic detectors has the benefit of versatility and selectivity, but is not associated with robustness, especially when organic molecules are employed, because in many cases electrons are required to flow through the organic medium, thus causing the destruction of the sensing element. In other cases, e.g., when no organic medium is employed, or when no electron flow through the organic medium takes place, sensitivity becomes the limiting parameter. Generally, sensitivity of sensors is proportional to the contact area of the sensitive surface, because the larger the area the higher the probability that a molecule or photon can be detected by the sensing surface. Thus, in general, sensitivity is assumed to scale with surface area.

In Molecular Controlled Semiconductor Resistors (MOCSER), the molecules are adsorbed directly on the surface of a semiconductor device [U.S. Pat. No. 6,433,356, Gartsman, K. et al., Chem. Phys. Lett., 283:301-306, 1998]. This is in contrast to most other devices, where the chemicals are adsorbed on the gate metal or insulator layer of a metal oxide FET (MOSFET), or on the surface metal of a Schottky diode. These devices have limiting sensitivity because of the insulating film of the MOSFET and/or the metal.

The combination between molecules and semiconductor devices is also relevant for biological systems, as it allows use of molecules irrespective of their ability to form good monolayers, their electrical conductivity or their stability against electron transport through them [Ashkenasy et al., Acc. Chem. Res., 35, 121-128, 2002]. The ability to affect electronic properties of a semiconductor surface by adsorption of layers of (organic) molecules has been demonstrated and used to achieve selectivity.

Apart from the MOCSER several molecular semiconductor sensors are known in the art. Chemically modified FET (CHEMFET) sensors are based on changes in the current passing through the device due to adsorption of molecules on the gate. Un-gated (open gate FET; OGFET) sensors or surface accessible FET (SAFET) sensors include molecules, which are adsorbed on the surface normally covered by the gate metal between the source and the drain. These types of sensors, however, suffer from over-sensitivity to electrical interference due to their open gate structure, leading to high noise levels compared to devices with channels completely covered by a gate oxide and/or metal.

Most prior art FET sensors use MOSFET-like structures because the relatively low barrier height that characterizes silicon devices leads to high leakage currents. An intrinsic problem one faces with MOSFET-like structures is that the oxidation layer on the surface reduces the sensitivity to adsorbed chemicals. This problem can be overcome by using molecular layers for both noise reduction (surface stabilization) and gating the FET, as disclosed in U.S. Pat. No. 6,433,356 and Gartsman et al. supra. Best results were obtained by constructing MOCSERs from special GaAs/(Al,Ga)As structures, which are similar to high electron mobility transistors, but without a gate electrode. Apart from the cost, use of GaAs and related materials leads to problems for in vivo use of such sensors and to ease of incorporation in present day Si-based electronic technologies.

There is thus a widely recognized need for, and it would be highly advantageous to have a molecular controlled electronic sensor, devoid of the above limitations.

SUMMARY OF THE INVENTION

According to one aspect of the present invention there is provided a semiconductor sensing device. The semiconductor sensing device comprises: (a) a device body made of at least two regions of semiconductor material forming at least one p-n junction thereamongst, wherein charge carrier concentrations of the at least two regions of semiconductor material are selected such that a current-voltage characteristic of the at least one p-n junction comprises a predetermined reverse breakdown voltage; and (b) at least one layer of molecules deposited on at least one of the at least two regions of the semiconductor material, the molecules being electrically-responsive to a species-of-interest in a manner such that when the molecules interact with the species-of-interest, the predetermined reverse breakdown voltage is modified.

According to further features in preferred embodiments of the invention described below, the regions of semiconductor material comprise a first region, a second region and a third region, the first region being made of a first type semiconductor material and the second and third regions being made of a second type semiconductor material.

According to still further features in the described preferred embodiments the second region is disposed on or formed in the first region so as to at least partially interpose between the first region and the third region.

According to still further features in the described preferred embodiments the semiconductor sensing device further comprises an additional electrode for electrically controlling the predetermined reverse breakdown voltage.

According to still further features in the described preferred embodiments the additional electrode at least partially engages a surface of the device body.

According to still further features in the described preferred embodiments the additional electrode is at least partially buried in the device body.

According to still further features in the described preferred embodiments the additional electrode comprises a perforated electrode disposed on the third region and being connectable to a voltage source.

According to still further features in the described preferred embodiments the additional electrode comprises a buried structure having a semiconductor electrode connectable to a voltage source and a semiconductor barrier, wherein the buried structure is formed in the device body in a manner such that the semiconductor electrode and the device body are interposed by the semiconductor barrier.

According to still further features in the described preferred embodiments the molecules are deposited on the third region.

According to still further features in the described preferred embodiments the semiconductor sensing device further comprises at least two conducting pads for connecting the device to a voltage source, wherein each conducting pad is formed in, attached to, or integrated with one region of the at least two regions of semiconductor material According to still further features in the described preferred embodiments the semiconductor sensing device further comprises a covering film deposited on at least one of the at least two regions.

According to another aspect of the present invention there is provided a method of manufacturing a semiconductor sensing device. The method comprises: (a) providing a device body and forming therein at least two regions of semiconductor material, so as to define at least one p-n junction, wherein charge carrier concentrations of the at least two regions of semiconductor material are selected such that a current-voltage characteristic of the at least one p-n junction comprises a predetermined reverse breakdown voltage; and (c) depositing at least one layer of molecules on at least one of the at least two regions of the semiconductor material, the molecules being electrically-responsive to a species-of-interest in a manner such that when the molecules interact with the species-of-interest, the predetermined reverse breakdown voltage is modified.

According to further features in preferred embodiments of the invention described below, the method further comprises depositing a covering film on at least one of the at least two regions.

According to still further features in the described preferred embodiments the method further comprises forming integrating or attaching the conducting pads to the at least two regions.

According to still further features in the described preferred embodiments the method further comprises forming an additional electrode in the device body for electrically controlling the predetermined reverse breakdown voltage.

According to still further features in the described preferred embodiments the formation of the additional electrode comprises depositing a perforated electrode on the third region in a manner such that the perforated electrode is connectable to a voltage source.

According to still further features in the described preferred embodiments the formation of the additional electrode comprises burying in the device body a semiconductor electrode and a semiconductor barrier in a manner such that the semiconductor electrode is connectable to a voltage source and the semiconductor barrier interposes between the semiconductor electrode and the device body.

According to yet another aspect of the present invention there is provided a method of sensing presence, absence or level of species-of-interest in the environment, the method comprising: (a) providing semiconductor sensing device having at least one layer of molecules deposited thereon, wherein the molecules are electrically-responsive to the species-of-interest in a manner such that when the molecules interact with the species-of-interest, a reverse breakdown voltage characterizing the semiconductor sensing device is modified; (b) applying a reverse bias to the semiconductor sensing device; (c) exposing the semiconductor sensing device to the environment; and (d) using the modifications in the reverse breakdown voltage for sensing presence, absence or level of the species-of-interest.

According to further features in preferred embodiments of the invention described below, the method further comprises placing an additional semiconductor sensing device in an isolated environment and comparing a reverse breakdown voltage of the additional semiconductor sensing device with the reverse breakdown voltage of the semiconductor sensing device.

According to still further features in the described preferred embodiments, the sensing of presence, absence or level of the species-of-interest comprises scanning a voltage of the applied reverse bias.

According to still further features in the described preferred embodiments the sensing of presence, absence or level of the species-of-interest comprises determining presence or absence of reverse current in a fixed voltage of the applied reverse bias.

According to still further features in the described preferred embodiments the interaction of the molecules with the species-of-interest comprises absorption of the species-of-interest by the molecules.

According to still further features in the described preferred embodiments the method further comprising heating the semiconductor sensing device so as to desorb the species-of-interest off the molecules.

According to still further features in the described preferred embodiments the semiconductor sensing device comprises a device body made of at least two regions of semiconductor material forming at least one p-n junction thereamongst, wherein charge carrier concentrations of the at least two regions of semiconductor material are selected such that a current-voltage characteristic of the at least one p-n junction comprises a predetermined reverse breakdown voltage.

According to still further features in the described preferred embodiments the molecules and the charge carrier concentrations are selected such that the modification of the reverse breakdown voltage is accompanied by generation of an avalanche current through the at least one p-n junction.

According to still further features in the described preferred embodiments the electrical response of the molecules is characterized in that a charge of the molecules and a respective region of the at least two regions is modified when the molecules interact with the species-of-interest.

According to still further features in the described preferred embodiments the electrical response of the molecules is characterized in that a dipole moment of the molecules and a respective region of the at least two regions is modified when the molecules interact with the species-of-interest.

According to still further features in the described preferred embodiments the molecules and the charge carrier concentration of the third region are selected such that a combination of the molecules and the third region is characterized by a predetermined dipole moment, the predetermined dipole moment being modified when the molecules interact with the species-of-interest.

According to still further features in the described preferred embodiments the charge carrier concentration of the first region of the first type semiconductor material is larger than the charge carrier concentration of the second and the third regions of the second type semiconductor material.

According to still further features in the described preferred embodiments a thickness of the second region is at least three times a characteristic Debye length thereof. According to still further features in the described preferred embodiments a thickness of the third region is from about two times to about five times a characteristic Debye length thereof.

According to still further features in the described preferred embodiments the second region describes a closed shape surrounding the third region of the second type semiconductor material. According to still further features in the described preferred embodiments the closed shape has a width of at least two times the characteristic Debye length of the second region. According to still further features in the described preferred embodiments the closed shape has an inner diameter of at least five times the characteristic Debye length of the second region.

The present invention successfully addresses the shortcomings of the presently known configurations by providing a molecular controlled electronic sensor that enjoys properties far exceeding the prior art.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1A:
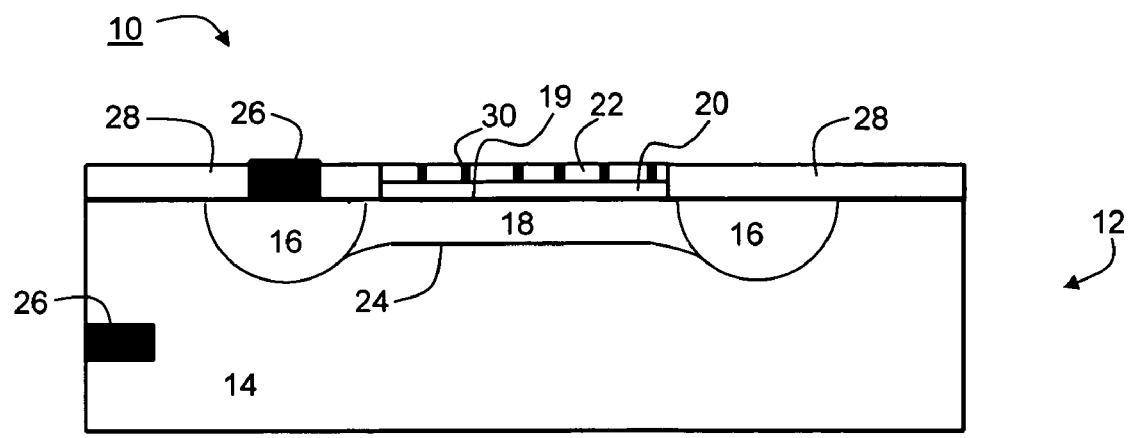
FIGS. 1a-b are schematic illustrations of a side view (FIG. 1a) and a top view (FIG. 1b) of a semiconductor sensing device, according to various exemplary embodiments of the present invention.

The present invention is of a molecular controlled semiconductor sensing device which can be used for sensitive and selective sensing of a variety of species-of-interests, such as, but not limited to, photons, chemical substances, biological materials and the like. Specifically, the present invention can be used to sense the species-of-interest by detecting modifications in a breakdown voltage characterizing the device.

The principles and operation of a semiconductor sensing device according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

While conceiving the present invention it was hypothesized and while reducing the present invention to practice it was realized that sensing of species-of-interest can be achieved using modifications of reverse breakdown voltage. Specifically, it was uncovered by the Inventors of the present invention that the characteristic reverse breakdown voltage of a semiconductor device varies when molecules deposited on the semiconductor device interact with the species-of-interest. Thus, according to one aspect of the present invention there is provided a semiconductor sensing device, referred to hereinafter as device 10.

Figure 1B:
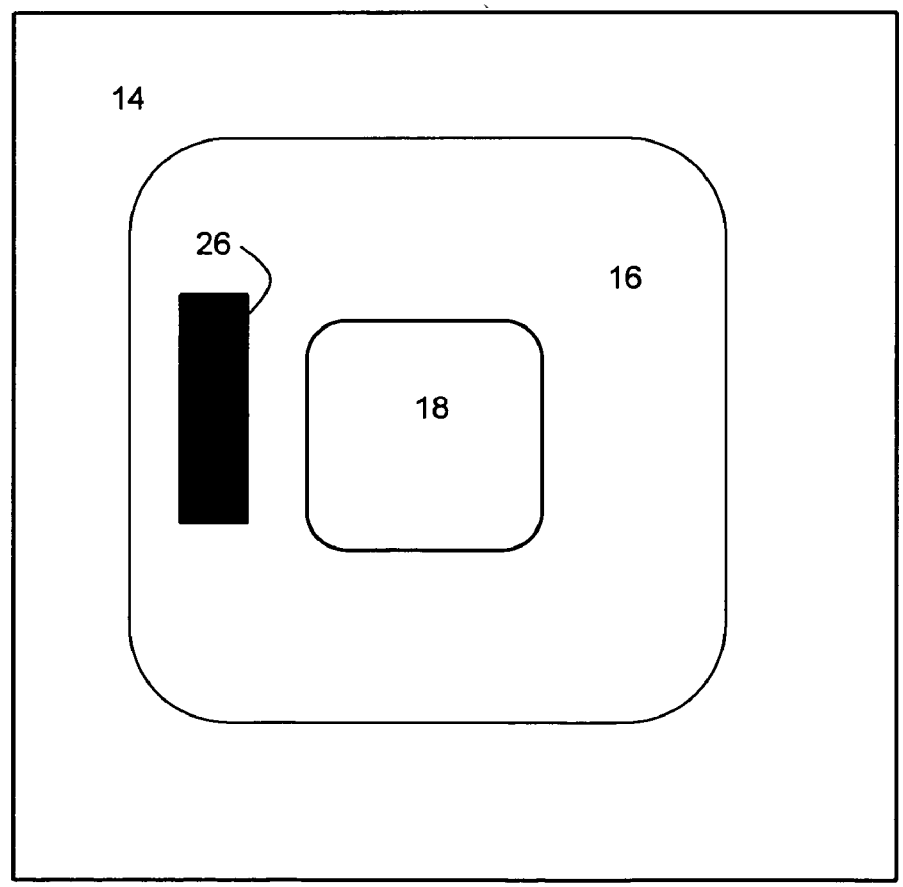

Referring now to the drawings, FIGS. 1a-b illustrate a side view (FIG. 1a) and a top view (FIG. 1b) of device 10, according to various exemplary embodiments of the present invention. In its simplest configuration, device 10 comprises a semiconductor device body 12 and one or more layers of molecules 20 which are electrically-responsive to a species-of-interest 22. Preferably, molecules 20 form a partial or complete monolayer on the surface of device 10. The electric response of molecules 20 is realized using the modification (increment or decrement) of a reverse breakdown voltage of device 10 upon interaction event with the species 22, either directly (voltage) or via the change in current at a given voltage.

Device body 12 is made of two or more regions of semiconductor material forming at least one p-n junction 24 thereamongst. In the exemplary configuration shown in FIGS. 1a-b, device 10 comprises a first region 14, a second region 16 and a third region 18. It is to be understood that other configurations having a different arrangement and/or a different number of regions are not excluded from the scope of the present invention.

According to various exemplary embodiments of the present invention, molecules 20 are deposited (e.g., adsorbed) on surface 19 of third region 18. Molecules 20 are preferably bifunctional in a sense that molecules 20 are capable of both chemically binding to surface 19 and interacting with species 22, e.g., by absorption or formation of a chemical bond. Representative examples of a chemical bond that can be established between molecules 20 and surface 19 or species 22 include, without limitation, a covalent bond, an electrostatic bond, a coordinate bond, a hydrogen bond and a van der Waals bond. Representative examples of molecules 20 include, without limitation, various chloro- and alkoxysilanes, such as 2,3-aminopropyltrimethoxy-silane (APTS); various carboxylic acids, such as tartartc, malonic and succinic acid, as well as their derivatives (e.g., 2,3-di(p-cyanobenzoyl)tartaric acid); various alkenes, phoponates, phosphates, thiols, sulfides and their derivatives (e.g., 4,5-di(p-cyano-benzoyloxy)-1,2-dithiane).

Molecules 20 and the surface to which they bind form a structure having electrostatic properties (e.g., charge concentration, dipole moment etc.), which preferably remain substantially constant as long as molecules 20 do not interact with the species-of-interest. Once molecules absorb photons or bind to another molecule, the electrostatic properties are modified resulting in a new electrostatic configuration of device 10 and, consequently, a modification of the reverse breakdown voltage.

As further exemplified in the example section that follows, the various regions of device 10 can be constructed such that the current-voltage characteristics of the p-n junction(s) comprise a predetermined reverse breakdown voltage. Specifically, by a judicious selection of the charge carrier concentrations of the semiconductor materials, a reverse breakdown voltage ranging from about 2 volts to about 20 volts can be obtained.

As used herein the term "about" refers to ±10%.

Sensing device 10 can operate in more than one way. In one preferred embodiment, device 10 operates similarly to a Zener diode, in which case the onset or cessation of a reverse current through device 10 is used to determine presence or absence of the species-of-interest. This operation resembles the operation of a Zener diode, which is typically used in electrical circuits as a dynamical on/off switch for the purpose of voltage stabilization.

Thus, according to the presently preferred embodiment of the invention, a reversebias is applied to device 10 to maintain a voltage drop across device 10. Preferably, the voltage drop is slightly above or slightly below the breakdown voltage, depending on the nature of the modification of the reverse breakdown voltage caused by the interactions between the deposited molecules and the species-of-interest.

For example, if the interaction increases the breakdown voltage, the existence of a reverse current can correspond to absence of the species-of-interest and the cessation of the reverse current can correspond to a detection event. This can be achieved by applying the reverse bias above the breakdown voltage, to allow a reverse current to flow through device 10. The level of applied reverse bias is preferably selected such that upon an interaction event, the breakdown voltage is increased to beyond the applied bias. Thus, in this embodiment, an interaction event results in a cessation of the reverse current, because the voltage drop on device 10 is no longer sufficient to allow breakdown.

Similarly, if the interaction between the molecules and the species decreases the breakdown voltage, the onset of the reverse current can correspond to a detection event. This can be achieved by applying the reverse bias below the breakdown voltage, such that upon an interaction event, the breakdown voltage is decreased to below the applied bias, resulting in an onset of reverse current through device 10.

In another embodiment, device 10 preferably has a time-dependent response, hence operates similarly to a diode in which the breakdown mechanism is due to the avalanche effect. Thus, according to the presently preferred embodiment of the invention, the molecules, the charge carrier concentrations and/or the thickness of the depletion region of the p-n junction(s) are selected such that the modification of the reverse breakdown voltage is accompanied by generation of an avalanche current through the p-n junction. This can be achieved by selecting a sufficiently wide p-n junction so as to allow the charge carriers to collide with lattice atoms. In this embodiment, the molecules are preferably selected such that their interaction decreases the breakdown voltage. In operation, a reverse bias, slightly below the breakdown voltage, is applied to device 10. Once an interaction event occurs, the breakdown voltage decreases to below the applied reverse bias and charge multiplication is triggered. The resulting avalanche current is proportional to the number of interactions and device 10 can be used as a differential sensor, which is sensitive both to the presence and to the level (e.g., number, concentration) of the species-of-interest.

In an additional, yet preferred, embodiment, the device is exposed to the species-of-interest, and the applied reverse bias is scanned over a predetermined voltage range so as to determine whether or not the reverse breakdown voltage is modified. In this embodiment the device does not have to be subjected to a reverse bias during the exposure. The scan over the voltage range can be done subsequently to the exposure. It is to be understood that scanning of the voltage contemporaneously with the exposure is also contemplated.

The semiconductor regions of device 10 can be made of any semiconductor, such as, but not limited to, those that have as their main constituent(s): Silicon, group IV alloys, or combinations of the III and V elements, the so-called III-V compounds, where the groups III, IV and V denote the Periodic Table elements: III=B, Al, Ga, In or Tl; IV=Si, Ge or C; and V=N, P, As, Sb or Bi. For example, according to various exemplary embodiments of the present invention, regions 14, 16 and 18 are made of crystalline silicon, whereby region 14 has p-type conductivity, and regions 16 and 18 have n-type conductivity. Alternatively, region 14 can have n-type conductivity, while regions 16 and 18 have p-type conductivity. In any event, the charge carrier concentrations of the regions, as stated, are selected to obtain the desired reverse breakdown voltage of device 10. The charge carrier concentrations of regions 14, 16 and 18 are denoted hereinunder by $N_1$, $N_2$ and $N_3$, respectively.

Second region 16 is preferably disposed on or formed in first region 14 so as to at least partially interpose between regions 14 and 18. Thus, according to various exemplary embodiments of the present invention region 16 describes a closed shape surrounding region 18. For example, region 16 can be shaped as a circular ring, a square collar and the like. The advantage of this configuration is that the ring-like shape of the region 16 substantially reduces edge effects resulting in a substantial reduction or elimination of the sensitivity of device 10 to surface conductivity. The thickness, width and inner diameter of region 16 are preferably substantially larger than its characteristic Debye length.

A Debye length can be defined as the distance in a semiconductor over which the local electric field affects the distribution of free charge carriers. The Debye length, L, is inversely proportional to the square root of the charge carrier concentration, N, and can be calculated from the following formula (in SI units):

$$L_i(N_i) = \sqrt{\frac{4\pi\varepsilon\varepsilon_0 kT}{q^2 N_i}}, \qquad (1)$$

where, $\varepsilon_0$ is the dielectric permittivity of vacuum, $\varepsilon$ is the dielectric constant of the semiconductor, q is the elementary charge, k is the Boltzmann constant and T the is temperature. The subscript i in Equation 1 above denotes the number of the semiconductor region. Thus, in the present embodiment, $L_1$, $L_2$ and $L_3$ correspond to the Debye lengths of first region 14, second region 16 and third region 18, respectively.

According to a preferred embodiment of the present invention, In any event, the dimensions of the semiconductor regions of device 10 are preferably selected so as to improve the signal to noise ratio. Thus, depending on the specific application for which device 10 is designed, the thickness of region 16 is preferably larger or equals $2L_2$, its width is from about $2L_2$ to about $8L_2$ and its inner diameter larger or equals $5L_2$. The thickness of region 18 is preferably from about $2L_3$ to about $5L_3$. It is to be understood that the above dimensions are not to be considered as limiting.

It was found by the inventors of the present invention that an optimal configuration can be achieved when the diameter of region 18 is about 1 micron.

Additionally, $N_2$, the charge carrier concentration of region 16 is preferably lower than both $N_1$ $_{and\ N3}$, the charge carrier concentrations of regions 14 and 18. For example, in various exemplary embodiments of the invention $N_1$ is selected to be on order of $10^{18}$ or more, e.g., from about $10^{18}$ to about $3 \times 10^{19}$ cm$^{-3}$, $N_2$ is about two orders of magnitude smaller than $N_1$, e.g., from about $1 \times 10^{16}$ cm$^{-3}$ to about $5 \times 10^{17}$ cm$^{-3}$ and $N_3$ is on the same order of magnitude as $N_2$ however larger, e.g., $N_3 \gtrsim 3N_2$. According to a preferred embodiment of the present invention the value of $N_3$ is selected in accordance with the desired level of breakdown reverse current. Specifically, lower doping of region 18 corresponds to a larger extent of the avalanche effect, hence higher attainable level of breakdown reverse current.

Referring now again to FIGS. 1*a-b*, device 10 preferably comprises at least two conducting pads 26 for connecting device 10 to a voltage source (not shown). Pads 26 can be formed in, attached to or integrated with the semiconductor regions of device 10. For example, in one embodiment, pads 26 are metal contacts prepared on the surfaces of regions 16 and 14, such that when pads 26 are connected to the voltage source, a reverse bias is established across junction 24. According to various exemplary embodiments of the present invention, device 10 further comprises a covering film 28 deposited on at least one of the regions. Preferable, molecules 20 remain exposed to allow them to interact freely with the species-of-interest. Thus, according to a preferred embodiment of the present invention film 28 covers regions 14 and 16 and exposes region 18. Film 28 can be any covering film known in the art, such as, but not limited to, silicon oxide, silicon nitride passivation layer and/or photoresist or similar polymer.

As stated, in various exemplary embodiments of the invention, device 10 is subjected to a reverse bias, either slightly above or slightly below the reverse breakdown voltage, depending on the nature and level of the modification to the breakdown voltage caused in response to the interaction with the species-of-interest. The reverse bias is preferably established between the n-type semiconductor regions (e.g., regions 16 and 18) and the p-type semiconductor regions (e.g., region 14).

According to a preferred embodiment of the present invention the characteristic reverse breakdown voltage of device 10 can also be controlled electrically. This embodiment is particularly useful when the extent of the breakdown voltage modification caused by certain species-of-interest and/or different types of molecules 20 is insufficient to generate detection event. The present embodiment therefore further improves the sensitivity of device 10 by allowing fine tuning of the characteristic reverse breakdown voltage.

The aforementioned electrical control can be achieved by providing one or more additional electrodes which, once connected to a voltage source, tune the characteristic reverse breakdown voltage of device 10 to desired level. This can be done in more than one way. For example, in one embodiment, the additional electrode preferably comprises a perforated electrode 30, disposed on third region 18. A voltage source is thus connected to pads 26 and perforated electrode 30. The characteristic reverse breakdown can be tuned by varying the potential of electrode 30.

Figure 2:
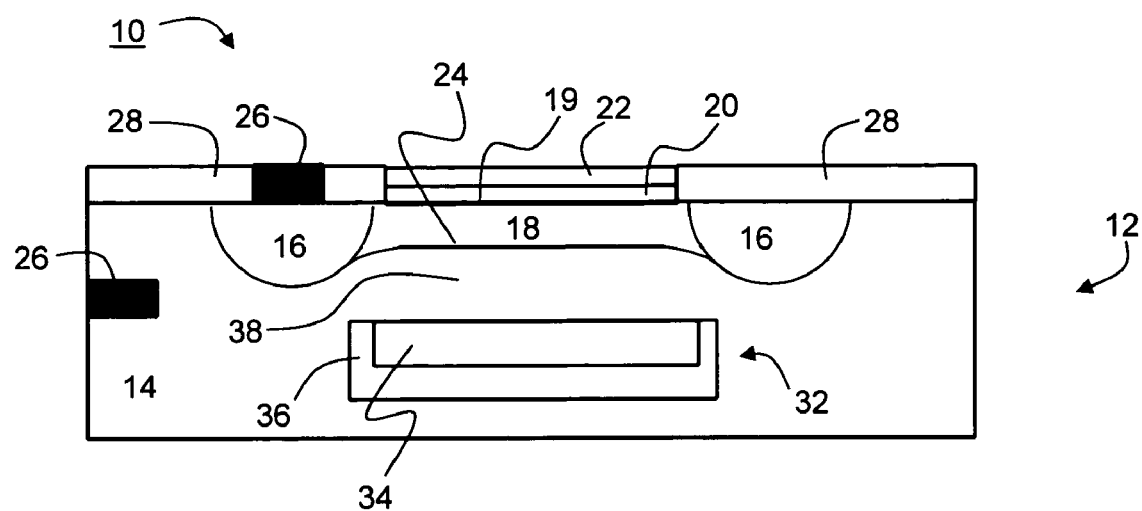
FIG. 2 is a schematic illustration of the semiconductor sensing device in a preferred embodiment in which a buried structure is employed.

Reference is now made to FIG. 2, which is a schematic illustration of device 10, according to another preferred embodiment of the present invention. Hence, in this embodiment, device 10 comprises a buried structure 32 formed in device body 12 having a semiconductor electrode 34 and a semiconductor barrier 36. Buried structure 32 serves for electrically controlling the characteristic reverse breakdown of device 10.

Both electrode 34 and barrier 36 of structure 32 are preferably of the same type semiconductor, preferably the opposite type of first region 14. According to a preferred embodiment of the present invention barrier 36 has a very low charge carrier concentration (e.g., $N < 5 \times 10^{16}$ cm$^{-3}$) and electrode 34 is more heavily doped (e.g., $N > 5 \times 10^{17}$). Thus, in this embodiment, barrier 36 serves as an insolating barrier between region 14 and electrode 36. The voltage source is thus connected to pads 26 and electrode 36, whereby the characteristic reverse breakdown is tuned by varying the potential of electrode 36. As will be appreciated by one ordinarily skilled in the art, the applied voltage affects the charge carrier concentration of a portion 38 of region 14, which is adjacent to region 18, thereby allowing the fine-tuning of the reverse breakdown voltage.

According to another aspect of the present invention, there is provided a method of sensing presence, absence or level of species-of-interest in the environment. The method comprises the following method steps, which are illustrated in the flowchart diagram of FIG. 3. It is to be understood, that unless otherwise defined, the method steps described hereinbelow can be executed either contemporaneously or sequentially in any combination or order of execution. Specifically, neither the ordering of the flowchart of FIG. 3, nor the numerals designating its various blocks are to be considered as limiting. For example, two or more method steps, appearing in the description or in the flowchart of FIG. 3 in a particular order, can be executed in a different order (e.g., a reverse order) or substantially contemporaneously.

Figure 3:
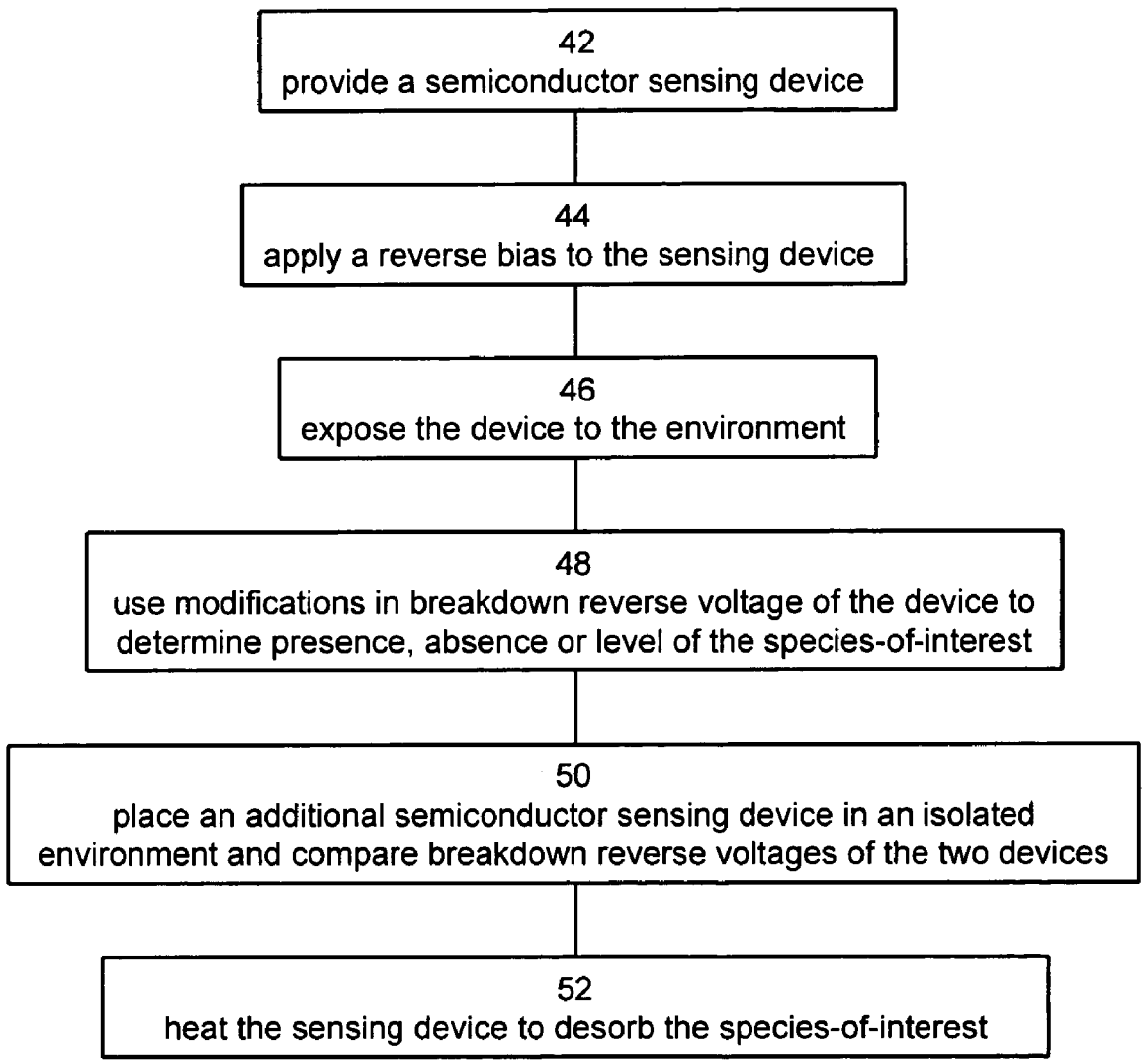
FIG. 3 is a flowchart diagram describing a method of sensing presence, absence or level of species-of-interest in the environment, according to various exemplary embodiments of the present invention.

Referring now to FIG. 3, in step 42 of the method a semiconductor sensing device (e.g., device 10) is provided and in step 44 a reverse bias is applied to the sensing device, as further detailed hereinabove. In step 46 of the method, the sensing device is exposed to the environment so as to allow the species (if present) to interact with the sensing element of the device (e.g., the aforementioned bifunctional molecules). The method continues to step 48 in which modifications in the reverse breakdown voltage of the device are used to sense the species-of-interest. The sensing can be done in more than one way. In one preferred embodiment, the voltage of the applied reverse bias is scanned so as to determine the breakdown voltage of the device, hence the presence, absence or level of the species-of-interest. In another embodiment, the reverse breakdown voltage modifications are monitored by determining presence or absence of reverse current while keeping the applied voltage fixed.

According to a preferred embodiment of the present invention the method comprises an additional step (step 50 in FIG. 3), in which two or more devices are used so as to decrease thermal drift of the measurements. Hence, according to the presently preferred embodiment of the invention an additional semiconductor sensing device (e.g., device 10) is placed in an isolated environment. The reverse breakdown voltage of the additional device is preferably compared with the reverse breakdown voltage of the exposed sensing device, for example, using an electrical bridge scheme.

In embodiments in which the sensing device is used to sense species-of-interest which are absorbed or bind by the sensing element of the device, the method preferably continues to step 52, in which the sensing element of the device is heated so as to desorb the species-of-interest. This embodiment is particularly useful when it is desired to reuse the device. The desorption of the species restores the original reverse breakdown voltage of the device, thus facilitating its reuse. The heating can be done by any way known in the art. A preferred heating procedure includes the exploitation of the breakdown current for heating, for example, by reducing the electrical resistance of the electrical circuit to which the device is connected.

Figure 4:
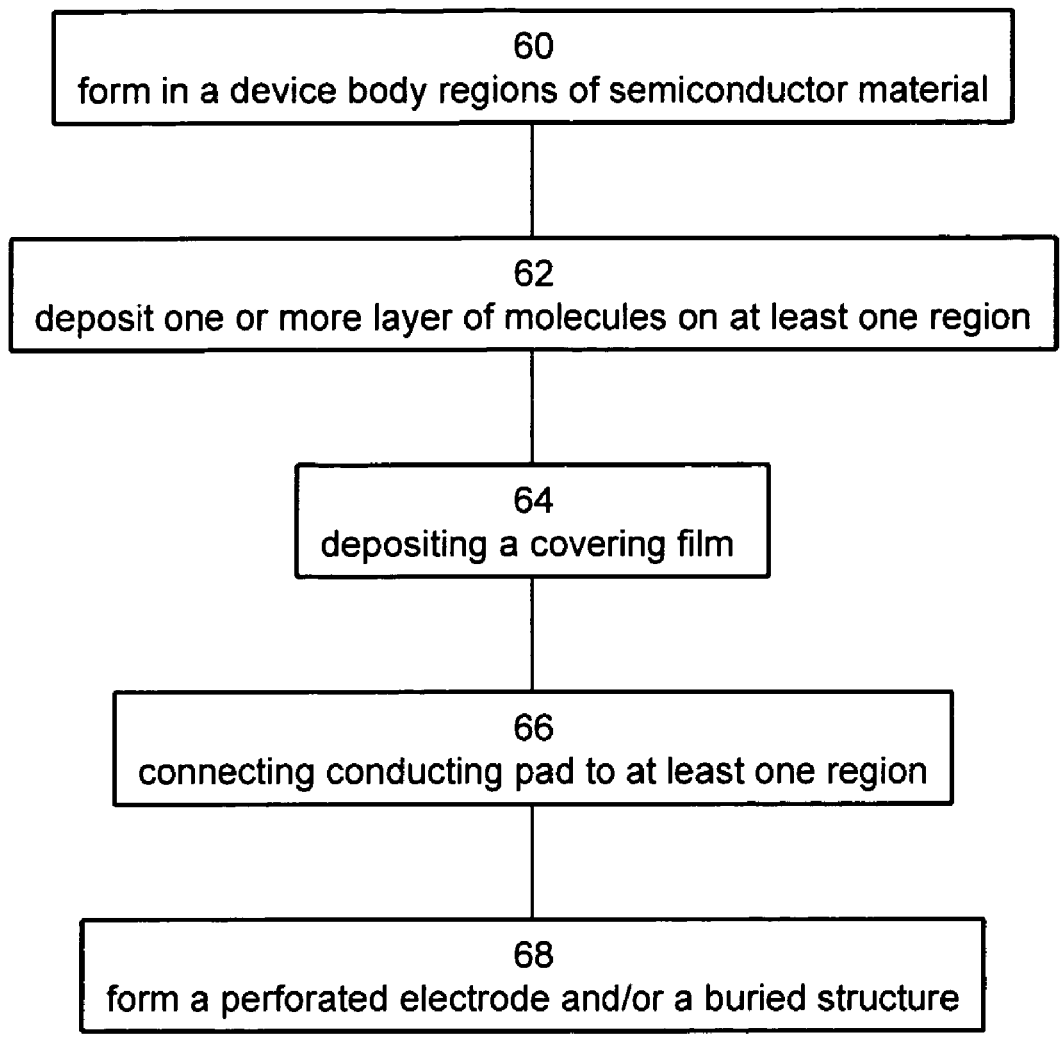
FIG. 4 is a flowchart diagram describing method of manufacturing a semiconductor sensing device, according to various exemplary embodiments of the present invention.

According to an additional aspect of the present invention, there is provided a method of manufacturing a semiconductor sensing device. The method comprises the following method steps, which are illustrated in the flowchart diagram of FIG. 4.

Similarly to FIG. 3 above, the method steps described hereinbelow can be executed either contemporaneously or sequentially in any combination or order of execution.

Hence, according to a preferred embodiment of the present invention the method starts at step 60 in which at least two regions of semiconductor material are formed in a device body. The charge carrier concentrations of formed regions are selected, as stated, to provide predetermined reverse breakdown voltage. The regions can be formed in the device body using any standard photolithographic and micro-machining technique known in the art.

In step 62, one or more layers of molecules which are electrically responsive to the species-of-interest are deposited on one or more of the semiconductor regions of the device as further detailed hereinabove. The method preferably continues to step 64 in which a covering film is deposited on selected regions of the device (e.g., regions 14 and 16). Additional steps of the method include, without limitations, the connection of conducting pads (step 66) and the formation of the perforated electrode and/or buried structure (step 68) as further detailed hereinabove.

Additional objects, advantages and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following example.

EXAMPLES

Reference is now made to the following examples, which, together with the above descriptions, illustrate the invention in a non limiting fashion.

Example 1

Theoretical Considerations

Current-Voltage Characteristics in the Absence of the Species-of-Interest

The voltage-current curve of device 10 before it is exposed to the species-of-interest is determined by the three contributions:

1. A surface leakage current.
2. A "generation" current of the p-n junction:

$$I_g \approx q n_i^2 \left[ A_{21}\left(\frac{D_1}{\lambda_1 N_1} + \frac{D_2}{L_2 N_2}\right) + A_{31}\left(\frac{D_1}{\lambda_1 N_1} + \frac{D_3}{\lambda_3 N_3}\right) \right] (A/cm^2), \quad (2)$$

where $A_{12}$ is the area between the first and second regions, $A_{13}$ is the area between the first and third regions, $D_i$ (i=1, 2, 3) is the diffusion coefficient of charged carries in the corresponding regions, $n_i$ is the intrinsic carrier concentration of the semiconductor, and $\lambda_i$ is the carrier diffusion length in the corresponding regions.

3. Tunneling current, mainly between the first and third regions, given by:

$$J \approx q \sqrt{\frac{kT}{2\pi m_1}} N_1 \cdot (A_{13}) \cdot \exp \quad (3)$$

-continued $$\left( -\frac{4}{3} \frac{\sqrt{2m}}{q\hbar} \frac{E_g^{3/2}}{V_a} \sqrt{\frac{q}{2\varepsilon\varepsilon_0(\phi_{bi}+V_a)} \frac{N_1 \cdot N_3}{N_1+N_3}} \right)(A/cm^2),$$

where $E_g$ is the band gap of the semiconductor, $\hbar$ is Planck constant, $V_a$ is the applied voltage, $\phi_{bi}$ is the built-in voltage drop between the first and third regions. The voltage drop $\phi_{bi}$ is given by:

$$\phi_{bi} \approx \frac{q}{kT} \ln\left(\frac{N_1 N_3}{n_i^2}\right). \quad (4)$$

Typically, when the applied bias is below the reverse breakdown voltage, the sum of the surface, generation and tunneling currents does not exceed a few tens of $\mu A/cm^2$.

On the other hand, if the applied bias exceeds a breakdown voltage, the current increases sharply and is limited only by a ballast resistor which protects the measuring circuit. The breakdown voltage, $V_b$, can be estimated as:

$$V_b \approx E_b \sqrt{\frac{q}{2\varepsilon\varepsilon_0(\phi_{bi}+V_a)} \frac{N_1 \cdot N_3}{N_1+N_3}} \approx \quad (5)$$

$$E_b \cdot \sqrt{\frac{qN_3}{2\varepsilon\varepsilon_0\left(\frac{q}{kT}\ln\left(\frac{N_1 N_3}{n_i^2}\right)+V_a\right)}}$$

where $V_a$ is the voltage level of the applied bias and $E_b$ is the breakdown electric field of the semiconductor. Typically, $E_b$ is about several 100 kV/cm and weakly depends on the concentration of the charge carriers.

As can be understood from Equation 5, the strong dependence of the reverse breakdown voltage on $N_3$ allows to accurately set the reverse breakdown voltage by selecting an appropriate value for $N_3$.

Figure 5:
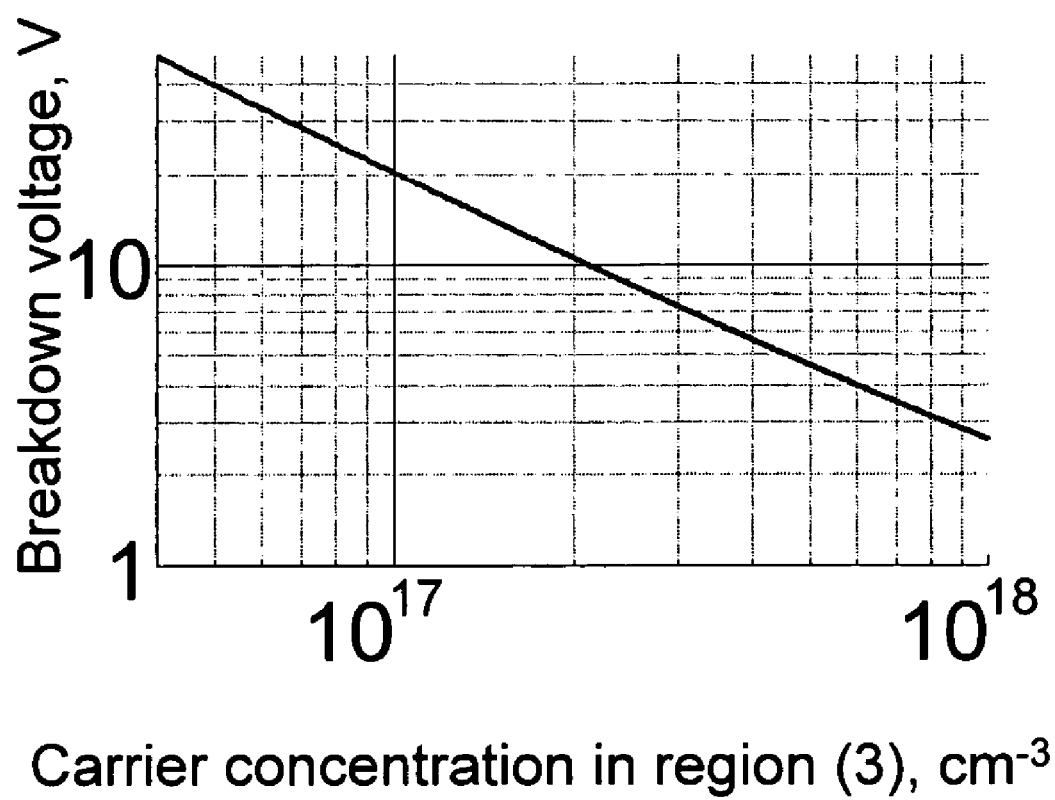
FIG. 5 shows the dependence of the reverse breakdown voltage on the charge carrier of one semiconductor region of the device.

FIG. 5 shows the dependence of the reverse breakdown voltage on $N_3$ for a silicon based device with $N_1=10^{19}$ cm$^{-3}$.

Effect of the Species of Interest on the Current-Voltage Characteristic

As stated, the species-of-interest can change the dipole moment of the structure formed by the molecules and the surface to which they bind. Many species-of-interest have a permanent dipole moment. Therefore, their interaction with the molecules affects the dipole moment of the molecules-surface structure. Adsorption of the species onto the molecule thus changes the electrical potential at the top surface of the third region and, thereby, also modifies the distribution of the charged carriers.

The effect of the molecules can be viewed as attraction or repulsion of the charged carriers to the surface of the third region. When the width of the third region is only a few Debye lengths, the interaction of the species-of-interest with the molecules-surface structure changes the concentration of the charged carriers near the p-n junction interposing the first and third regions, leading to a change of the breakdown voltage.

The sensitivity of the device, in volts per monolayer of absorbed molecules, can be understood as follows. A monolayer of small organic absorbed molecules corresponds to a surface density, $S_m$, of about $10^{14}$ molecules/cm$^{-2}$. The ability of the molecules to attract or to repel the electrons towards the surface is a function of the total dipole moment of the molecule-surface structure. A typical value of the attraction or to repulsion ability, c, is larger than or equal to about $10^{-3}$ electrons per molecule.

A monolayer covering f=1% of the surface thus leads to the redistribution of $\approx 10^{10}$ electrons/cm$^2$. The total concentration of electrons per unit area in the third region is given by $d_3 \cdot N_3 \approx 10^{11}-10^{13}$ cm$^{-2}$. Therefore, 1% of a monolayer causes a change of about 0.1-10% in the electron concentration in the third region. As will be appreciated by one ordinarily skilled in the art, such a change is sufficient to modify the reverse breakdown voltage.

The responsivity, R, in volts per monolayer is given by $$R = \frac{\partial V_r}{\partial N_3} \frac{c S_m}{d_3}$$

and is in the range of 0.3 to 30 volts per monolayer, depending on the doping level and the thickness of the third region. For example, for $N_3=10^{17}$ cm$^{-3}$ and $d_3=80$ nm the responsivity is about 180 millivolts per monolayer. The sensitivity of the device is defined by the accuracy with which the breakdown voltage can be measured. Presently available measuring devices can measure a breakdown voltage as low as 100 microvolts, corresponding to a sensitivity of about 0.001% of a monolayer. The accuracy of the measurements of the breakdown voltage depends on the electrical noise in the device. The electrical noise, in its turn, depends on the resistances of regions 16 and 18. Therefore, the final dimensions of the semiconductor regions depend on the specific applications for which the device is designed.

Example 2

Prototype Device

A device was prepared in accordance with FIGS. 1a-b. The device had a sensitivity of about 1 volts per monolayer with respect to succinic acid.

First region 14 was a p-type semiconductor and second 16 and third 18 regions were each n-type semiconductor. The charge carrier concentrations regions 14, 16 and 18 were, respectively: $N_1=10^{19}$ cm$^{-3}$, $N_2=5\times 10^{16}$ cm$^{-3}$ and $N_3=5\times 10^{17}$ cm$^{-3}$. The area of third region 18 was 4 μm$^2$. Molecules 20 were prepared by treating the SiO$_x$ (1.5 nm) on Si surface with 3-aminopropyltrimethoxy-silane solution for 20 min at room temperature.

Exposure of the device to 0.2 mM solution of succininc acid caused a shift of the breakdown voltage from 4.65 volts to 5.40 volts. Assuming complete coverage, one can deduce that the sensitivity of the device was close to 1 volt per monolayer.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A semiconductor sensing device, comprising:
   (a) a device body made of at least a first region a second region and a third region forming at least one p-n junction thereamongst, said first region being made of a first type semiconductor material and said second and said third regions being made of a second type semiconductor material wherein charge carrier concentrations of said regions of said semiconductor materials are selected such that a current-voltage characteristic of said at least one p-n junction comprises a predetermined reverse breakdown voltage;
   (b) at least one layer of molecules deposited on at least one of said regions of said semiconductor materials, said molecules being electrically-responsive to a species-of-interest being at least one of a photon, a chemical substance and a biological material in a manner such that upon exposure of the device to said species-of-interest, said molecules interact with said species-of-interest, and said predetermined reverse breakdown voltage is modified; and
   (c) a perforated electrode disposed on said third region and being connectable to a voltage source, for electrically controlling said predetermined reverse breakdown voltage.

2. The device of claim 1, wherein said molecules and said charge carrier concentrations are selected such that said modification of said reverse breakdown voltage is accompanied by generation of an avalanche current through said at least one p-n junction.

3. The device of claim 1, wherein said electrical response of said molecules is characterized in that a charge of said molecules and a respective region of said regions of semiconductor materials is modified when said molecules interact with said species-of-interest.

4. The device of claim 1, wherein said electrical response of said molecules is characterized in that a dipole moment of said molecules and a respective region of said regions of semiconductor materials is modified when said molecules interact with said species-of-interest.

5. The device of claim 1, further comprising a covering film deposited on at least one of said regions of semiconductor materials.

6. The device of claim 1, further comprising at least two conducting pads for connecting the device to a voltage source, wherein each conducting pad of said at least two conducting pads is formed, attached or integrated with one region of said regions of semiconductor material.

7. The device of claim 1, further comprising an additional electrode for electrically controlling said predetermined reverse breakdown voltage.

8. The device of claim 7, wherein said an additional electrode comprises a buried structure having a semiconductor electrode connectable to a voltage source and a semiconductor barrier, wherein said buried structure is formed in said device body in a manner such that said semiconductor electrode and said device body are interposed by said semiconductor barrier.

9. The device of claim 1, wherein said molecules are capable of both chemically binding to a surface of said at least one region and interacting with said species-of-interest by absorption or formation of a chemical bond.

10. The device of claim 1, further comprising:
(d) an electronic unit configured for detecting said modification of said reverse breakdown voltage thereby to sense said species-of-interest.

11. The device of claim 1, wherein said second region is disposed on or formed in said first region so as to at least partially interpose between said first region and said third region.

12. The device of claim 11, wherein said molecules are deposited on said third region.

13. The device of claim 12, wherein said molecules and said charge carrier concentration of said third region are selected such that a combination of said molecules and said third region is characterized by a predetermined dipole moment, said predetermined dipole moment being modified when said molecules interact with said species-of-interest.

14. The device of claim 13, wherein said charge carrier concentration of said first region of said first type semiconductor material is larger than said charge carrier concentration of said second and said third regions of said second type semiconductor material.

15. The device of claim 13, wherein a thickness of said third region is from about two times to about five times a characteristic Debye length thereof.

16. The device of claim 13, wherein a thickness of said second region is at least three times a characteristic Debye length thereof.

17. The device of claim 16, wherein said second region describes a closed shape surrounding said third region of said second type semiconductor material.

18. The device of claim 17, wherein said closed shape has a width of at least two times said characteristic Debye length of said second region.

19. The device of claim 17, wherein said closed shape has an inner diameter of at least five times said characteristic Debye length of said second region.

20. A semiconductor sensing device, comprising:
(a) a device body made of at least a first region a second region and a third region forming at least one p-n junction thereamongst, said first region being made of a first type semiconductor material and said second and said third regions being made of a second type semiconductor material, wherein charge carrier concentrations of said first said second and said third regions are selected such that a current-voltage characteristic of said at least one p-n junction comprises a predetermined reverse breakdown voltage; and
(b) at least one layer of molecules deposited on said third region, said molecules and said charge carrier concentration of said third region being selected such that a combination of said molecules and said third region is characterized by a predetermined dipole moment;
wherein said molecules are electrically-responsive to a species-of-interest being at least one of a photon, a chemical substance and a biological material in a manner such that when said molecules interact with said species-of-interest said predetermined dipole moment and said predetermined reverse breakdown are modified.

21. A method of sensing presence, absence or level of species-of-interest in the environment, the species-of-interest being at least one of a photon, a chemical substance and a biological material, the method comprising:

(a) providing semiconductor sensing device having:
(i) a device body made of at least a first region a second region and a third region forming at least one p-n junction thereamongst, said first region being made of a first type semiconductor material and said second and said third regions being made of a second type semiconductor material wherein charge carrier concentrations of said regions of said semiconductor materials are selected such that a current-voltage characteristic of said at least one p-n junction comprises a predetermined reverse breakdown voltage;
(ii) at least one layer of molecules deposited on at least one of said regions of said semiconductor materials, wherein said molecules are electrically-responsive to the species-of-interest in a manner such that when said molecules interact with the species-of-interest, said predetermined reverse breakdown voltage is modified; and
(iii) a perforated electrode disposed on said third region and being connectable to a voltage source, for electrically controlling said predetermined reverse breakdown voltage:
(b) applying a reverse bias to said semiconductor sensing device;
(c) exposing said semiconductor sensing device to the environment; and
(d) using modifications in said reverse breakdown voltage for sensing presence, absence or level of the species-of-interest.

22. The method of claim 21, further comprising placing an additional semiconductor sensing device in an isolated environment and comparing a reverse breakdown voltage of said additional semiconductor sensing device with said reverse breakdown voltage of said semiconductor sensing device.

23. The method of claim 21, wherein said sensing of said presence, absence or level of the species-of-interest comprises scanning a voltage of said applied reverse bias.

24. The method of claim 21, wherein said presence, absence or level of the species-of-interest comprises determining presence or absence of reverse current in a fixed voltage of said applied reverse bias.

25. The method of claim 21, wherein said interaction of said molecules with the species-of-interest comprises absorption of the species-of-interest by said molecules.

26. The method of claim 21, further comprising heating said semiconductor sensing device so as to desorb the species-of-interest off said molecules.

27. The method of claim 21, wherein said molecules and said charge carrier concentrations are selected such that said modification of said reverse breakdown voltage is accompanied by generation of an avalanche current through said at least one p-n junction.

28. The method of claim 21, wherein said electrical response of said molecules is characterized in that a charge of said molecules and a respective region of said regions of said semiconductor materials is modified when said molecules interact with said species-of-interest.

29. The method of claim 21, wherein said electrical response of said molecules is characterized in that a dipole moment of said molecules and a respective region of said regions of said semiconductor materials is modified when said molecules interact with said species-of-interest.

30. The method of claim 21, wherein said semiconductor sensing device further comprises a covering film deposited on at least one of said regions of said semiconductor materials.

31. The method of claim 21, wherein said semiconductor sensing device further comprises at least two conducting pads for connecting the device to a voltage source, each conducting pad of said at least two conducting pads being formed in, attached to, or integrated with one region of said regions of said semiconductor materials.

32. The method of claim 21, wherein said semiconductor sensing device further comprises an additional electrode for electrically controlling said predetermined reverse breakdown voltage.

33. The method of claim 32, wherein said additional electrode at least partially engages a surface of said device body.

34. The method of claim 33, wherein said additional electrode is at least partially buried in said device body.

35. The method of claim 33, wherein said additional electrode comprises a buried structure having a semiconductor electrode connectable to a voltage source and a semiconductor barrier, wherein said buried structure is formed in said device body in a manner such that said semiconductor electrode and said device body are interposed by said semiconductor barrier.

36. The method of claim 21, wherein said second region is disposed on or formed in said first region so as to at least partially interpose between said first region and said third region.

37. The method of claim 36, wherein said molecules are deposited on said third region.

38. The method of claim 37, wherein said molecules and said charge carrier concentration of said third region are selected such that a combination of said molecules and said third region is characterized by a predetermined dipole moment, said predetermined dipole moment being modified when said molecules interact with said species-of-interest.

39. The method of claim 38, wherein said charge carrier concentration of said first region of said first type semiconductor material is larger than said charge carrier concentration of said second and said third regions of said second type semiconductor material.

40. The method of claim 38, wherein a thickness of said third region is from about two times to about five times a characteristic Debye length thereof.

41. The method of claim 38, wherein a thickness of said second region is at least three times a characteristic Debye length thereof.

42. The method of claim 41, wherein said second region describes a closed shape surrounding said third region of said second type semiconductor material.

43. The method of claim 42, wherein said closed shape has a width of at least two times said characteristic Debye length of said second region.

44. The method of claim 42, wherein said closed shape has an inner diameter of at least five times said characteristic Debye length of said second region.

* * * * *